United States Patent
Yoon et al.

(10) Patent No.: US 10,976,257 B2
(45) Date of Patent: Apr. 13, 2021

(54) PIXEL CIRCUIT AND METHOD FOR OPTICAL SENSING

(71) Applicant: The Regents of the University of Michigan, Ann Arbor, MI (US)

(72) Inventors: Euisik Yoon, Ypsilanti, MI (US); Jihyun Cho, Cupertino, CA (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 1027 days.

(21) Appl. No.: 15/176,980

(22) Filed: Jun. 8, 2016

(65) Prior Publication Data

US 2016/0356718 A1 Dec. 8, 2016

Related U.S. Application Data

(60) Provisional application No. 62/172,728, filed on Jun. 8, 2015.

(51) Int. Cl.
| | |
|---|---|
| G01J 1/42 | (2006.01) |
| G01J 1/44 | (2006.01) |
| G01J 1/02 | (2006.01) |
| G01N 21/64 | (2006.01) |
| A61B 5/00 | (2006.01) |
| H03M 3/00 | (2006.01) |
| A61B 5/145 | (2006.01) |
| A61B 5/1455 | (2006.01) |
| A61B 5/01 | (2006.01) |
| H03M 1/46 | (2006.01) |

(52) U.S. Cl.
CPC ....... *G01N 21/6456* (2013.01); *A61B 5/0071* (2013.01); *G01J 1/02* (2013.01); *G01J 1/42* (2013.01); *G01J 1/44* (2013.01); *G01N 21/6408* (2013.01); *H03M 3/464* (2013.01); *A61B 5/01* (2013.01); *A61B 5/14539* (2013.01); *A61B 5/14546* (2013.01); *A61B 5/14552* (2013.01); *H03M 1/466* (2013.01); *H03M 3/426* (2013.01)

(58) Field of Classification Search
CPC ............ G01N 21/6456; G01N 21/6408; A61B 5/0071
USPC ....................................................... 250/362
See application file for complete search history.

(56) References Cited

U.S. PATENT DOCUMENTS 7,897,928 B2 * 3/2011 Kaufmann ........ H01L 27/14601
250/370.08

OTHER PUBLICATIONS

Marmarelis "Identification of Nonlinear Biological Systems Using Laguerre Expansions of Kernels." Annals of Biomedical Engineering, vol. 21, 1993, pp. 573-589.
Itatani, et al. "Attosecond Streak Camera." Physical Review Letters, vol. 88, No. 17, Apr. 29, 2002, 4 pages, doi:10.1103/PhysRevLett.88.173903.

(Continued)

*Primary Examiner* — David P Porta
*Assistant Examiner* — Carolyn Fin
(74) *Attorney, Agent, or Firm* — Reising Ethington P.C.

(57) ABSTRACT

A pixel circuit that includes: a substrate body having a channel influenced by an electric field; an aperture in communication with the channel for receiving a fluorescent light input and moving electrons through the substrate body; and a plurality of sampling devices adapted to be switched on simultaneously to sample the moving electrons.

16 Claims, 5 Drawing Sheets

(56) References Cited

OTHER PUBLICATIONS

Webb, S. E. D., et al. "A wide-Field time-Domain fluorescence lifetime imaging microscope with optical sectioning." Review of Scientific Instruments, vol. 73, No. 4, 2002, pp. 1898-1907., doi:10.1063/1.1458061.

Kavusi, et al. "On incremental sigma-Delta modulation with optimal filtering." IEEE Transactions on Circuits and Systems I: Regular Papers, vol. 53, No. 5, May 2006, pp. 1004-1015., doi:10.1109/tcsi.2006.870218.

Li, et al. "Hardware implementation algorithm and error analysis of high-Speed fluorescence lifetime sensing systems using center-of-Mass method." Journal of Biomedical Optics, vol. 15, No. 1, Jan./Feb. 2010, 10 pages, doi:10.1117/1.3309737.

Suh, et al. "Column-Parallel Correlated Multiple Sampling Circuits for CMOS Image Sensors and Their Noise Reduction Effects." Sensors, vol. 10, 2010, pp. 9139-9154., doi:10.3390/s101009139.

Sun, et al. "Fluorescence lifetime imaging microscopy for brain tumor image-Guided surgery." Journal of Biomedical Optics, vol. 15, No. 5, Sep./Oct. 2010, 5 pages, doi:10.1117/1.3486612.

Zlatanski, et al. "Streak camera in standard (Bi)CMOS (bipolar complementary metal-oxide-semiconductor) technology." Measurement Science and Technology, vol. 21, 2010, 13 pages, doi:10.1088/0957-0233/21/11/115203.

Won, et al. "Precision and accuracy of the analog mean-delay method for high-speed fluorescence lifetime measurement." Journal of the Optical Society of America A, vol. 28, No. 10, Oct. 2011, pp. 2026-2032.

Oike, et al. "A 256×256 CMOS image sensor with $\Delta\Sigma$-Based single-Shot compressed sensing." 2012 IEEE International Solid-State Circuits Conference, 2012, 3 pages, doi:10.1109/isscc.2012.6177057.

Tyndall, David, et al. "A 100Mphoton/s time-Resolved mini-Silicon photomultiplier with on-Chip fluorescence lifetime estimation in 0.13μm CMOS imaging technology." 2012 IEEE International Solid-State Circuits Conference, 2012, 3 pages, doi:10.1109/isscc.2012.6176946.

Seo, Min-Woong, et al. "A Low-Noise High Intrascene Dynamic Range CMOS Image Sensor With a 13 to 19b Variable-Resolution Column-Parallel Folding-Integration/Cyclic ADC." IEEE Journal of Solid-State Circuits, vol. 47, No. 1, Jan. 2012, pp. 272-283., doi:10.1109/jssc.2011.2164298.

Oike, et al. "CMOS Image Sensor With Per-Column $\Sigma\Delta$ ADC and Programmable Compressed Sensing." IEEE Journal of Solid-State Circuits, vol. 48, No. 1, Jan. 2013, pp. 318-328., doi:10.1109/jssc.2012.2214851.

Niclass, et al. "A 100m-Range 10-Frame/s 340×96-Pixel time-of-Flight depth sensor in 0.18μm CMOS" IEEE Journal of Solid-State Circuits, vol. 48, No. 2, Feb. 2013, pp. 559-572., doi:10.1109/esscirc.2011.6044926.

Cho, et al. "A 3-D Camera With Adaptable Background Light Suppression Using Pixel-Binning and Super-Resolution." IEEE Journal of Solid-State Circuits, vol. 49, No. 10, Oct. 2014, pp. 2319-2332., doi:10.1109/jssc.2014.2340377.

Field, et al. "A 100 fps, Time-Correlated Single-Photon-Counting-Based Fluorescence-Lifetime Imager in 130 nm CMOS." IEEE Journal of Solid-State Circuits, vol. 49, No. 4, Apr. 2014, pp. 867-880., doi:10.1109/jssc.2013.2293777.

Marcu, et al., Fluorescence lifetime spectroscopy and imaging: principles and applications in biomedical diagnostics., CRC Press, 2014, 570 pages.

* cited by examiner

PIXEL CIRCUIT AND METHOD FOR OPTICAL SENSING

CROSS-REFERENCE TO RELATED APPLICATION

This application claims the benefit of U.S. Provisional Application No. 62/172,728 filed Jun. 8, 2015, the entire contents of which are hereby incorporated by reference.

TECHNICAL FIELD

The present invention relates to pixel circuits for optical sensing, and more particularly, to pixel circuits used for real-time fluorescence lifetime imaging.

BACKGROUND

Time-resolved active imaging captures snapshots of fast-varying transient optical signals. This imaging technique has extensively been used in a number of biomedical, scientific and engineering studies. For example, it is applied to 3-D image sensors where the imaging system measures the time-of-flight (TOF) of photons to provide the depth information. This can provide a three-dimensional visual perception that can be utilized for navigation or collision avoidance. In biomedical fields, fluorescence lifetime imaging microscopy (FLIM) allows measurements of various cellular-level biological features such as pH, temperature, oxygen and ion concentration. FLIM also has been applied in intra-operative imaging techniques to help surgeons distinguish cancer cells from normal cells for precision incision and removal (i.e., of the cancer cells).

Although a number of studies have shown that time-resolved active imaging is feasible in some applications, it is not feasible in applications requiring high-imaging speed. For example, real-time imaging is desirable in vivo imaging, where the imaged object and the camera are typically moving. In such cases, motion may cause image-blur and distortion. In addition, high frame-rates are desirable for redundant imaging (e.g., wherein the imaging is repeated for robustness and reliability). For example, the images may be taken repeatedly from different spectral components (hyperspectral) or from different distances (optical sectioning). Thus, a multivariate analysis may provide a better contrast for the sensor.

However, conventional fluorescence lifetime imagers cannot provide real-time images. The image acquisition may take tens of seconds or even a few minutes. Additionally, post-processing or analysis may tack on another minute of processing. Therefore, a low cost, high speed and compact time-resolved imager is needed for widespread use of the technique in the real world.

Existing time-resolved imaging methods for fluorescence lifetime imaging include: time-correlated single photon counting (TCSPC), time-gated imaging, and a streak camera imaging. Each is discussed below.

TCSPC uses a single photon detector such as photon-multiplier-tube (PMT) or single-photon avalanche diode (SPAD). For the measurement, the photon detection rate may be reduced to around 1% to provide a single photon incident, or else the detector may miss photons after the initially received photon. At the arrival of each photon, the single photon detector triggers time-to-digital converter (TDC) to measure the photon arrival time. Repeating this will resolve the time of each of the individual photons. TCSPC with SPAD offers sub-nanosecond resolution and a large array implementation (e.g., using CMOS technology). TCSPC has slow acquisition speed because of the low photon detection probability. TCSPC implementations can improve the overall acquisition speed (409 k pixel/s) as in; however, handling large data-rates (e.g., 42 Gbps) may require complicated and expensive equipment (e.g., including 4× PC cards).

Time-gated imaging employs either an electronic shutter implemented using CMOS technology or an image intensifier having an optical shutter. Time-gating can be a high-speed technique (e.g., having multiple photon detection capability); however, photon loss occurs due to shutter operation (e.g., while the shutter opens and closes). In addition, the time resolution is typically worse than TCSPC due to a finite width of the time gate.

In streak camera imaging, incoming photons at different times are mapped at different locations. A tube is used to achieve this time-to-space conversion in three steps: a photon-to-electron conversion, an electron deflection by time-varying electric field, and an electron-to-photon conversion. Since the timing is spatially resolved at the tube, any suitable image sensor may be used. An image sensor with 2-D pixel array can provide a 1-D line image as the other dimension may be used for timing information. This technique provides good timing resolution down to an atto-second but is typically complex and costly. Also, the principle of streak camera (i.e., time-to-space conversion) has proven difficult to implement in integrated circuits without using the streak tube. While some integrated streak cameras claim to be tube-less (e.g., for the cost reduction purposes), these cameras are not truly tube-less and exhibit highly lossy behavior, as well as low sensitivity.

Thus, fast fluorescence lifetime imaging has been achieved using time-gated imaging with two time gates and a lifetime estimation algorithm called rapid lifetime determination (RLD). This method measures the minimum information (i.e., two values) for the lifetime estimation. Due to this small data amount, the data acquisition, conversion and processing can be performed quickly. However, this technique lacks sufficient dynamic range for many applications (e.g., the method only works well within a narrow range of determinable lifetimes).

The disclosure below discusses high-speed time-resolved image sensors for real-time fluorescence lifetime imaging (e.g., CMOS). A high-speed solution is presented—e.g., photon acquisition and data handling such as conversion, transmission and processing. In addition, a center-of-mass method (CMM) is employed, which offers a wide dynamic range.

SUMMARY

According to one aspect of the invention, there is provided a method of optical imaging using a pixel circuit for use in fluorescence lifetime imaging. The method includes the steps of: receiving at a pixel circuit a fluorescent light input emitted from a material; receiving two electrical outputs from the pixel circuit in response to the light input; performing a center-of-mass method (CMM) calculation using the two electrical outputs; and determining a lifetime parameter ($\tau$) based on the CMM calculation.

According to another aspect of the invention, there is provided a pixel circuit. The pixel circuit includes: a substrate body having a channel configured to be influenced by an electric field; an aperture in communication with the channel such that a fluorescent light input received by the aperture causes electrons to move along the channel through the substrate body in the presence of the electric field; and a plurality of sampling devices spaced along the channel and adapted to be switched on simultaneously so that the pixel circuit samples the moving electrons at different locations along the channel.

According to another aspect of the invention, there is provided an analog-to-digital (ADC) circuit. The analog-to-digital (ADC) circuit includes: a coarse resolution ADC circuit; and a fine resolution ADC circuit, wherein the fine resolution ADC circuit includes a charge redistribution digital-to-analog converter (DAC).

According to yet another aspect of the invention, there is provided a method of compression for use in fluorescence lifetime imaging. The method includes the steps of: receiving at an analog-to-digital conversion (ADC) circuit an input from a pixel circuit; determining a coarse resolution value using a coarse resolution circuit, wherein the coarse resolution includes determining a weighted sum of a finite number of samples; determining a fine resolution value using a fine resolution circuit; and providing the fine and coarse resolution values as an output.

According to another aspect of the invention, there is provided a method of compression for use in fluorescence lifetime imaging. The method includes the steps of: receiving at an analog-to-digital conversion (ADC) circuit an input from a pixel circuit; determining a coarse resolution value using a coarse resolution circuit; determining a fine resolution value using a fine resolution circuit, wherein determining the fine resolution value comprises using a charge redistribution digital-to-analog converter (DAC) to minimize a quantity of ADC cycles; and providing the fine and coarse resolution values as an output.

BRIEF DESCRIPTION OF THE DRAWINGS

One or more embodiments of the invention will hereinafter be described in conjunction with the appended drawings, wherein like designations denote like elements, and wherein.

DESCRIPTION OF THE ILLUSTRATED EMBODIMENTS

Figure 1A:
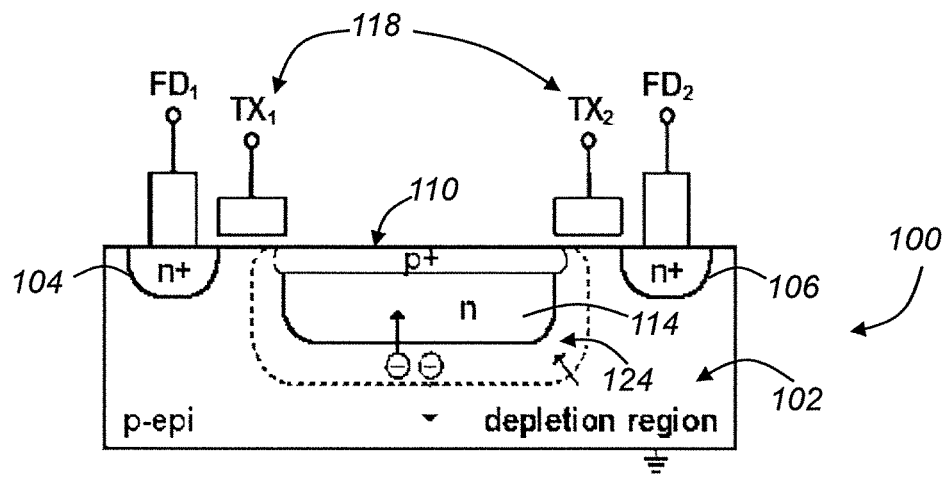
FIG. 1A illustrates a pixel circuit constructed in accordance with an embodiment of the invention.

Several circuits and methods relating to pixel elements are described herein, including: a method of estimating a fluorescence lifetime using pixel-level processing, a multi-tap pixel circuit and associated method of operation; and a compressive analog-to-digital conversion (ADC) circuit and associated method of operation. The method of estimating the fluorescence lifetime ($\tau$) using pixel-level processing is suitable for instances of single exponential decay. The multi-tap pixel circuit and the compressive ADC circuit are suitable for use when (1) the number of photons is limited due to the photo-bleaching; and (2) resolving multiple fluorescence lifetimes from complex exponential decay (e.g. bi-exponential decay).

Estimating a Fluorescence Lifetime ($\tau$) Using Pixel-level Processing

In at least one embodiment, the fluorescence lifetime ($\tau$) from a single exponential decay of a material may be determined using a center-of-mass method (CMM). And once the lifetime ($\tau$) is known, the material's properties may be identified using the lifetime ($\tau$). The material may be illuminated (e.g., active imaging) in order to receive a fluorescent light input (e.g., one or more photons) onto a pixel from the material. The CMM may measure the mean value of the photon arrival times (e.g., also known as an analog mean delay (AMD) method). In one embodiment, the CMM includes fluorescence decay with a single exponential. The waveform of the fluorescence is expressed with single lifetime ($\tau$) as Equation (1).

$$f(t)=A\cdot\exp(-t/\tau),\qquad\qquad\text{Equation (1)}$$

where, A is the intensity of the fluorescence. The lifetime ($\tau$) may be calculated as the mean value of the function normalized by the function itself, as shown in Equation (2).

$$\tau = \frac{\int t\cdot f(t)\,dt}{\int f(t)\,dt} \qquad\qquad\text{Equation (2)}$$

The CMM processor may be implemented 'on-chip'; see, for example, D. Tyndall, B. Rae, D. Li, J. Richardson, J. Arlt, and R. Henderson, "A 100Mphoton/s time-resolved mini-silicon photomultiplier with on-chip fluorescence lifetime estimation in 0.13 µm CMOS imaging technology," in 2012 IEEE International Solid-State Circuits Conference, 2012, pp. 122-124, the contents of which are hereby incorporated by reference. The sensor measures the waveform, f(t), using TCSPC. The digital data is then processed by digital summation for the integral in the Equation (2). A discrete time version of Equation (2) is shown in Equation (3) with normalization by a sampling period $\Delta$.

$$\frac{\tau}{\Delta} = \frac{\sum n\cdot f[n]}{\sum f[n]} \qquad\qquad\text{Equation (3)}$$

While the computation or calculation of the CMM is relatively simple, a significant volume of data may be processed in order to determine or measure the properties of the material. This may affect the overall frame-rate. Thus, to enhance the frame-rate, CMM processing may be performed before any analog-to-digital conversion (e.g., in the analog-domain). More specifically, CMM processing may be performed in the charge domain. In order to implement Equation (2) or Equation (3), the analog processor may require a multiplier (e.g., a circuit device capable of performing a multiplication function; e.g., a Gilbert cell) in order to calculate $t \cdot f(t)$ or $n \cdot f[n]$. Skilled artisans will appreciate that this may prove challenging provided the current state of technology—e.g., especially in light of the desired timing constraints (which are on the order of nanoseconds). According to at least one implementation of fluorescence lifetime ($\tau$), a multiplier is not required; e.g., the calculation may be multiplier-free by using estimation shown in Equation (4). For example, instead of adding the multiplied samples in time domain as in (3), the weighted sum may be expanded into multiple terms of integration, repeating the measurement with a shifting of a time window as shown in Equation (4).

$$\Sigma n \cdot f[n] = [\int_0^T f(t)dt + \int_\Delta^T f(t)dt + \ldots + \int_{T-\Delta}^T f(t)dt],  \quad \text{Equation (4)}$$

where, n=1 ... N, T=N·$\Delta$, and N is the number of sampling periods ($\Delta$) to be evaluated, and T is a period between light/energy excitation pulses on the imaged material.

Using Equation (4) may be particularly desirable for pixel-level implementations where the pixel size is relatively small (e.g., in the order of 10 μm×10 μm).

Figure 1B:
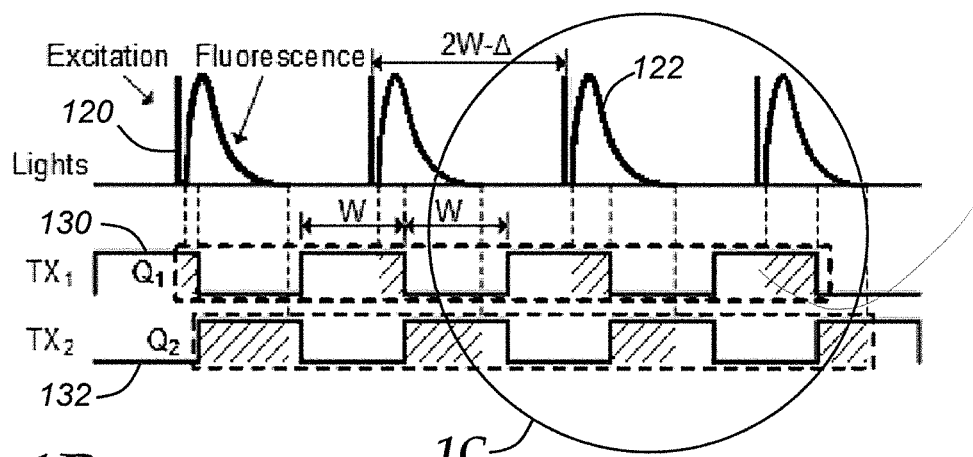
FIG. 1B depicts a timing diagram associated with operation of the pixel circuit of FIG. 1A.
Figure 1C:
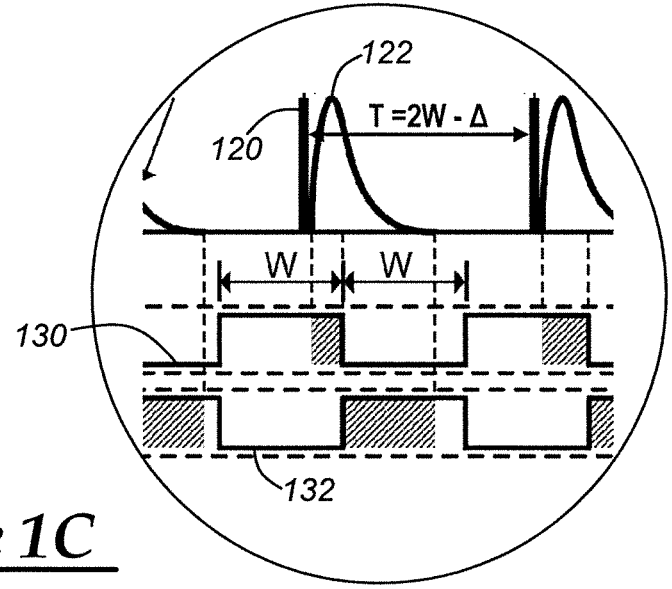
FIG. 1C is an enlarged view of a portion of the timing diagram of FIG. 1B.

FIG. 1A illustrates one embodiment of a pixel circuit 100 with timing control and FIGS. 1B and 1C depict a sample timing diagram associated with the pixel circuit 100. The illustrated pixel circuit 100 includes a substrate body 102 coupled to two transfer gates (TX$_1$, TX$_2$) and two floating diffusion taps or integration storages (FD$_1$, FD$_2$). The substrate body 102 is comprised of two "n+" regions 104, 106 and a middle region 110 comprising a "p+" region 112 and an "n" region 114—the "n+" regions 104, 106 spaced from one another by the middle region 110. One "n+" region 104 is in electrical contact with tap1 (FD$_1$) while the other "n+" region 106 is in electrical contact with tap2 (FD$_2$). Further, transfer gate (TX$_1$) is located proximate to tap1 (FDA and transfer gate (TX$_2$) is located proximate to tap2 (FD$_2$). Skilled artisans will appreciate that the pixel circuit 100 of FIG. 1A is a semiconductor device implemented as a variation of what is commonly referred to as a pinned photodiode. It can be fabricated using a CMOS Image Sensor (CIS) process, using a standard CMOS process along with another process used for pinned photodiodes. In this embodiment, the two transfer gates (TX$_1$, TX$_2$) collectively operate as a time-gating device 118.

During operation, a number of excitation pulses 120 (e.g., having period (T), FIG. 1C) may be provided at a target (e.g., the object to be imaged) (not shown) by a light or energy source (e.g., a laser or transmitter, not shown). The target may be a material such as biological tissue. In response to the excitation pulses 120, a fluorescent response may be induced at the target. This response may be absorbed as a fluorescent light input in the middle region 110 of the pixel circuit 100 (FIGS. 1B and 1C illustrate the response and its decay 122). During absorption, the middle region 110 behaves as a depletion region 124, as illustrated, thereby enabling electrons (i.e., photocurrent) to move through the depletion region 124 to the "n+" regions 104, 106, as discussed below. This absorption may occur concurrently with triggering or clocked signals 130, 132 being received at the pixel circuit 10 via gates (TX$_1$, TX$_2$). During clock pulse windows (W) that are high (i.e., "1") via gate TX$_1$, the photocurrent may be integrated at tap FD$_1$; and during clock pulse windows (W) that are high (i.e., "1") via gate TX$_2$, the photocurrent may be integrated at tap FD$_2$.

FIGS. 1B and 1C illustrate the clocked signals 130, 132 as square waves (however, this is merely an example; other implementations also exist). In addition, the square wave provided via TX$_1$ may be shifted with respect to the square wave provided via TX$_2$—e.g., the rising edge of one clocked signal (TX$_1$) may or may not coincide with the falling edge of the other clocked signal (TX$_2$). It should be appreciated that the duration of the windows (W) may vary in other implementations. Further, the period (T) of the excitation pulses 120 may vary as well.

A difference or sampling period ($\Delta$) may be defined by the difference between each cycle of the clocked signal (2W) and the period (T) of the excitation pulses 120. Thus, sampling period ($\Delta$) may equal one cycle of the clocked signal (2W) less the period (T) of the excitation pulses 120 or $\Delta=2W-T$. Thus, as shown in FIG. 1C, T may equal $T=2W-\Delta$. Returning to Equation (4), these values of T and $\Delta$ may be used in the upper and lower limits of the estimation—e.g., $\inf_\Delta^T f(t)dt + \int_{2\Delta}^T f(t)dt + \ldots + \int_{T-\Delta}^T f(t)dt$.

In one embodiment, the CMM calculation is performed using integrations of the electrical values received via the taps (FD$_1$ or FD$_2$) with respect to the time-shifted windows (W). More specifically, the CMM calculation evaluates the integrations of each window (W) (or the area under each window) which coincide with the generated photocurrent (see FIGS. 1B and 1C). Each of these integrations are then summed as Q$_1$ and Q$_2$, as shown in Equations (5.1) and (5.2).

$$Q_1 = \int_0^\Delta f(t)dt + \int_0^{2\Delta} f(t)dt + \ldots + \int_0^{T-\Delta} f(t)dt = \Sigma(N-n) \cdot f[n] \quad \text{Equation 5.1}$$

$$Q_2 = \int_0^T f(t)dt + \int_\Delta^T f(t)dt + \ldots + \int_{T-\Delta}^T f(t)dt = \Sigma n \cdot f[n] \quad \text{Equation 5.2,}$$

where N equals T/$\Delta$. Thus, summations (Q$_1$ and Q$_2$) each estimate a measured charge of the light inputs. Then, the determination of the lifetime ($\tau$) is made using a CMM equation shown as Equation (6).

$$\tau = \frac{\sum n \cdot f[n]}{\sum f[n]} \cdot \Delta \cong \frac{Q_2}{(Q_1+Q_2)/N} \cdot \Delta = \frac{Q_2}{Q_1+Q_2} \cdot T \quad \text{Equation (6)}$$

Once the lifetime ($\tau$) has been determined, one or more properties of the target material may be determined using the lifetime parameter ($\tau$), as will be known to those skilled in the art. Thus, there has been described a method for estimating a lifetime ($\tau$) using a center-of-mass method (CMM) for a wide dynamic range in fluorescence lifetime imaging. The pixel-level CMM estimation is suitable for high speed imaging. One method for determining this estimation uses a two-tap pixel circuit and a controlled, predetermined timing scheme. The shifting gate integration calculates a CMM equation without a multiplier. The method described herein provides a wider dynamic range than the conventional RLD algorithm, without compromising the frame-rate.

Multi-tap Pixel Circuit and Associated Method of Operation for High-Photon Economy In many medical applications (e.g., such as in vivo measurements), the number of photons of the fluorescent light input (e.g., from the fluorescent response) is small because the power of the excitation light/energy is relatively small. For example, it may not be desirable for the excitation light to heat up the living tissue (e.g., to avoid damaging the tissue). Also, in some applications, higher intensity and higher frequency excitation lighting results in photo bleaching—e.g., the permanent loss of the fluorescence from the fluorescent substance. In these instances, attaining a high signal-to-noise ratio (SNR) from a limited number of photons is particularly desirable. As will be appreciated by skilled artisans, this is commonly referred to as photon economy (e.g., the ratio of the error and a minimum achievable error, which is a theoretical limit when photon shot noise is considered), where the smaller the photon economy, the better (e.g., the smallest value (1) being the theoretical minimum).

One method of achieving better photon economy is to provide high time-resolution (i.e., finely quantizing the time during photon acquisition). Conventionally, CMOS-gated imaging systems provide two-gated images (which corresponds to 1-bit quantization in time). And in order to operate, the transfer gates and integration nodes are placed relatively near the photodiode. To obtain higher resolution in such systems, additional gates (and gated images) would need to be used; however, only a limited number of these additional gates could be placed relatively near the photodiode. Thus, conventional systems using this technique and arrangement exhibit lower resolution, which may be undesirable. In the embodiment discussed below, a pixel circuit having more than two gates (and more than two taps) is disclosed which offers desirable photon economy, high-speed imaging capability, and high resolution which is not currently available (e.g., using known TCSPC or two-gated imaging systems).

Figure 2:
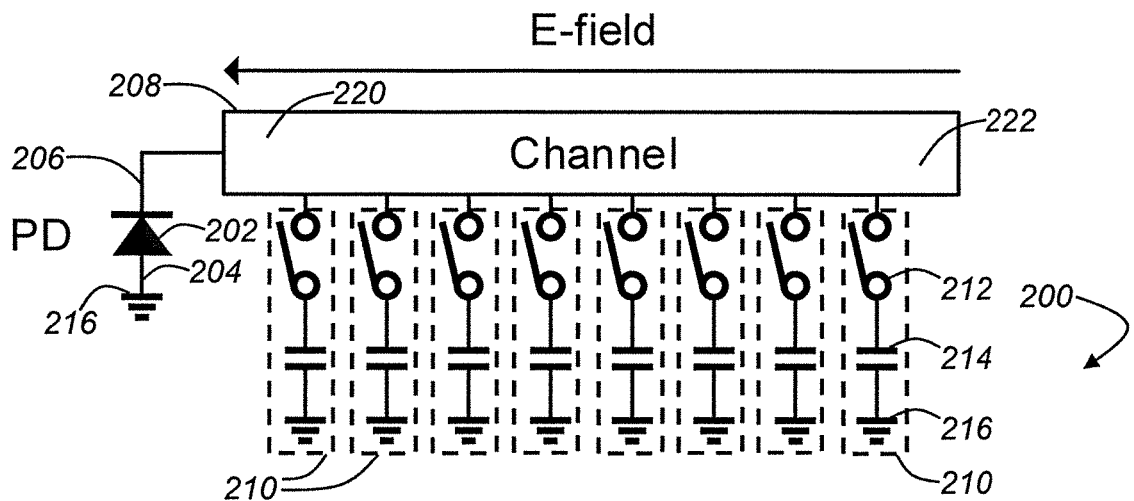
FIG. 2 illustrates a schematic diagram of a multi-tap pixel circuit.

FIG. 2 illustrates a schematic diagram of one embodiment of a multi-tap pixel circuit 200. The multi-tap pixel circuit 200 comprises a photo detector (PD) 202 coupled to ground 216 on one end 204 and coupled at an opposing end 206 to an extending channel 208 which may be influenced by an electric field (E-field or in other implementations a magnetic field or the like), and eight sampling devices 210 (each of which comprises a switch 212 and a capacitor 214 in series, the switch 212 being coupled to the channel 208 and the capacitor 214 being coupled to ground 216). It will be appreciated that more or fewer than eight sampling devices 210 is possible in other implementations. The E-field is biased so that photo-generated electrons received in the photodiode 202 drift from a proximate end 220 of the channel 208 (nearer the PD 202) to a distal end 222 of the channel 208. In some implementations, this drift occurs at a constant velocity for a time-to-space conversion; however, non-constant velocity implementations also exist (e.g., along the channel 208, or with respect to time (t)). The time-to-space conversion assumes that firstly generated electrons will drift farther toward the distal end 222 than the electrons which are generated later. The sampling devices 210 are spaced at different locations along at least a portion of the length of the channel 208. For example, as shown, they may be equally spaced along the length of channel 208 from the proximal end 220 to the distal end 222. As will be described more below, while the photo-generated electrons drift toward the distal end 222 (e.g., some being nearer the proximate end 220 and some nearer the distal end 222), the sampling devices 210 simultaneously open and collect or sample the spatially-distributed electrons. It is presumed that those electrons which are nearer to a given sampling device 210 than others will be collected by that particular sampling device. Thus, by initiating the collection of electrons by the spaced sampling devices 210 at the same time, the pixel circuit 200 records the distribution of electrons which, in effect, samples the electrons in the time-domain.

Figure 3A:
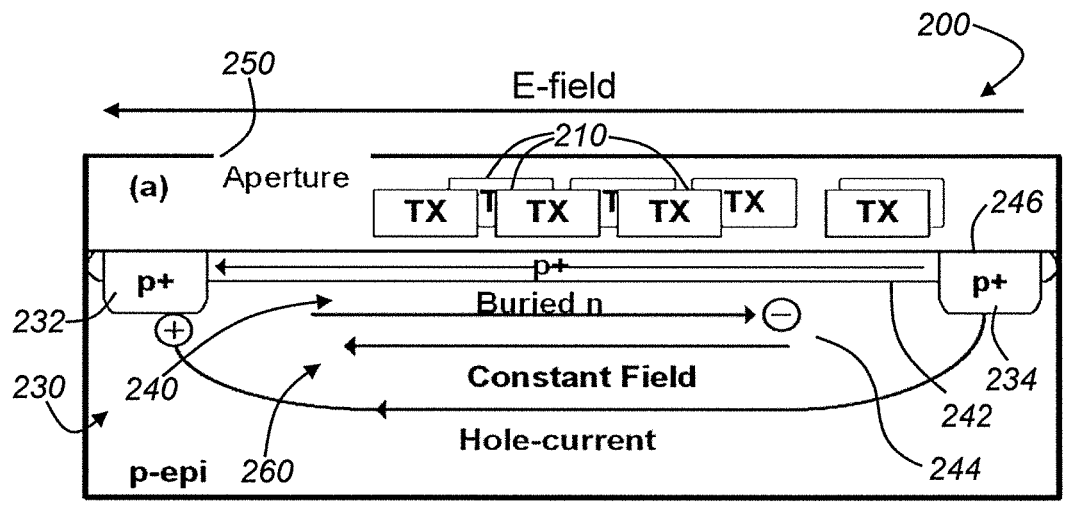
FIG. 3A illustrates one embodiment of the multi-tap pixel circuit schematically shown in FIG. 2.
Figure 3B:
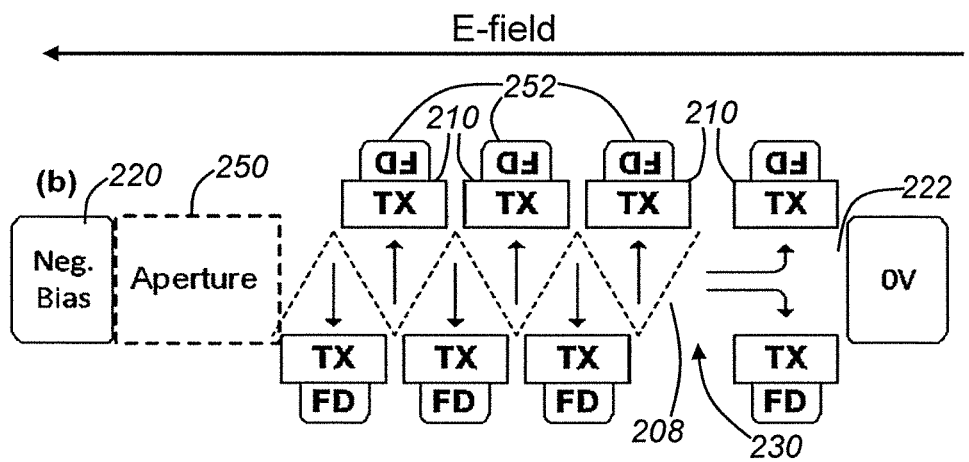
FIG. 3B illustrates another view of the multi-tap pixel circuit schematically shown in FIG. 2.

FIGS. 3A-3B illustrate two additional diagrams of the pixel circuit 200 shown in FIG. 2. For example, FIG. 3A (a sectional view) illustrates a substrate body 230 (e.g., comprised of silicon) having two "p+" regions 232, 234 (e.g., to provide ohmic contacts for the hole-current) spaced from another by a middle region 240 (which may become depleted similar to the depletion region 124 described above with respect to FIG. 1). The middle region 240 includes a "p+" region 242 and a buried "n-type" region 244 (e.g., where buried means isolated from a surface 246 of the silicon body 230).

Pixel circuit 200 may be fabricated as a semiconductor device using a CIS process as noted above in connection with FIG. 1. It may include an aperture 250 for receiving photon-generated electrons, as shown in FIGS. 3A-3B. Additionally, the illustrated pixel circuit 200 comprises eight floating diffusion taps (FD) 252 (shown in FIG. 3B) and the eight sampling devices (TX) 210 (FIGS. 3A-3B). Each tap (FDs) 252 includes an "n+" region (hidden in FIG. 3A) and the capacitors 214 (of FIG. 2) represent the capacitance between each FD 252 and the substrate body 230. It will be appreciated that the quantity (eight) is merely an example; other quantities of transfer gates (TX) 210 and taps (FD) 252 are also possible. FIG. 3A illustrates an constant electrical field along the channel 208 (i.e., the same E-Field shown in FIG. 2). FIG. 3B schematically illustrates four gates (TX) and four taps (FD) on one side of the channel and four gates (TX) and four taps (FD) on other side—the proximate end 220 of the channel 208 having a negatively biased voltage and the distal end 222 being 0 volts (V).

During the operation, one or more excitation pulses may be provided at a target (e.g., the object to be imaged) (not shown) by a light or energy source (e.g., a laser or transmitter, not shown). In response to the excitation pulse(s), a fluorescent response may be induced at the target. This response may be absorbed as a fluorescent light input (e.g., electrons) at the aperture 250 of the pixel circuit 200. Thus, the E-field is activated so that the electrons drift from the proximate end 220 of the channel 208 toward the distal end 222 (e.g., at a constant speed)—the "n-type" region 244 (now biased) becomes fully depleted (so that a depletion region 260 extends over the substrate body 230 between the two "p+" regions 232, 234. Initially, all gates (TX) 210 are closed or OFF so that no electrons are being sampled or collected. The potential gradient caused by a hole-current makes a potential gradient in the "n-type" buried channel 244. The buried "n-type" region 244 may be fully-depleted, and hence the potential is pinned relative to the potential of the nearby p-type region (e.g., in the middle region 240) (reference about pinned-photodiode: E. R. Fossum and D. B. Hondongwa, "A Review of the Pinned Photodiode for CCD and CMOS Image Sensors," *IEEE J. Electron Devices Soc.*, vol. 2, no. 3, pp. 33-43, May 2014.). In other words, the buried n-type region 244 also has the potential gradient as the p-type region but the p-type region is completely depleted. When an adequate number of electrons have been received into the channel 208 via the aperture 250, the gates (TX) 210 are triggered (e.g., for a window of time again) and the distributed electrons are sampled via taps (FDs) 252, as illustrated in FIG. 3B.

The sampled analog quantities (i.e. charges in FDs) next are converted (analog-to-digital conversion or ADC) and thereafter evaluated. An ADC circuit is discussed in greater detail below. From the digitized sampling measurements, the characteristics of the light input may be re-constructed. For example, a graphical depiction of the fluorescence intensity and decay can be determined. From this information, it will be appreciated that the lifetime (τ) can be determined (e.g., extracted, measured, or otherwise estimated).

Compressive A/D Conversion Circuit for High Speed Imaging and Method of Operation As previously discussed, in order to decrease processing time, the CMM calculation (or lifetime estimation) occurred prior to the analog-to-digital conversion. Processing speed can be improved depending upon the manner of the analog-to-digital conversion as well.

Figure 4:
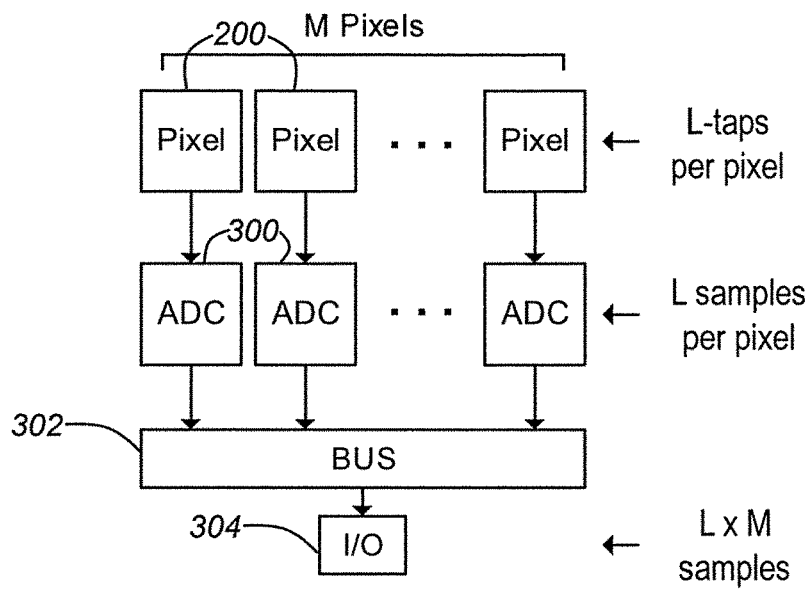
FIG. 4 illustrates a schematic diagram of a plurality of pixel circuits and analog-to-digital converters (ADCs) coupled to a communication bus and input/output circuit.

FIG. 4 illustrates a quantity (M) of pixel circuits 200, each being coupled to an associated ADC circuit 300. In addition, each ADC circuit 300 is coupled to a communication bus 302 enabling input and output at an I/O circuit 304. Processing speed depends at least partially upon the data-rate of each ADC circuit 300 and I/O circuit 304. As shown in FIG. 4, the data-rate can be expressed as L×M per frame, where L is the number of taps 252 per pixel circuit 200 and also the number of samples each ADC 300 is configured to process, and where M is the number of pixel circuits 200 and the number of ADC circuits 300. Thus, continuing with the example described and shown above (e.g., FIG. 3B illustrating pixel circuit 200 having eight taps (FDs) 252), the ADC circuit 300 would be capable of processing eight samples from each of the eight taps 252). It will be appreciated that the data converted by the ADCs may then be collected and serialized by the I/O circuit 304 and provided to another electronic module or circuit (not shown). Further, it should be appreciated that increasing the number of taps per pixel circuit increases the data-rate in all ADC circuits—consequently, this increases the resolution and processing time. In the column-parallel architecture shown in FIG. 4, the ADC conversion time is independent from the number (M) of pixel circuits 200 whereas the I/O processing time is proportional to the number (M) of pixel circuits 200.

The multi-tap pixel circuit 200 illustrated in FIGS. 3A-3B may produce at least an order of magnitude more data than the two-tap pixel circuit 100 shown in FIG. 1. This significantly increased data-rate may affect negatively the overall imaging speed due to finite bandwidth of the A/D conversion, data transmission, and signal processor. Thus, data compression is desirable.

Mixed-signal data compression implemented in A/D conversion is suitable for high speed imaging techniques—e.g., enabling both real-time imaging while still maintaining a desirable resolution. The CMM equation discussed above (see Equation (3)) may be used to reduce the number of samples. This equation is rewritten below.

$$\frac{\tau}{\Delta} = \frac{\sum n \cdot f[n]}{\sum f[n]} = \frac{1 \cdot f[1] + 2 \cdot f[2] + L \cdot f[L]}{f[1] + f[2] + \ldots + f[L]} \quad \text{Equation (7)}$$

In at least one embodiment, the numerator and denominator are calculated during the analog-to-digital conversion, and the I/O circuit 304 provides only two values. For example, the I/O circuit 304 may provide only the numerator and denominator instead of sending L values thereby improving I/O circuit processing time.

In one implementation, the numerator and denominator may be weighted sums of the L samples. Integrating or multiple-sampling ADCs such as incremental Sigma Delta ADC or folding ADC may perform the weighted sum during the conversion. Examples of Incremental Sigma Delta ADC methods are described in S. Kavusi, H. Kakavand, and A. E. Gamal, "On incremental sigma-delta modulation with optimal filtering," IEEE Trans. Circuits Syst. I Regul. Pap., vol. 53, no. 5, pp. 1004-1015, May 2006, and Y. Oike and A. El Gamal, "CMOS Image Sensor With Per-Column ΣΔ ADC and Programmable Compressed Sensing," IEEE J. Solid-State Circuits, vol. 48, no. 1, pp. 318-328, Jan. 2013. Examples of folding ADC methods are described in M.-W. Seo, S.-H. Suh, T. Iida, T. Takasawa, K. Isobe, T. Watanabe, S. Itoh, K. Yasutomi, and S. Kawahito, "A Low-Noise High Intrascene Dynamic Range CMOS Image Sensor With a 13 to 19b Variable-Resolution Column-Parallel Folding-Integration/Cyclic ADC," IEEE J. Solid-State Circuits, vol. 47, no. 1, pp. 272-283, Jan. 2012, and S. Suh, S. Itoh, S. Aoyama, and S. Kawahito, "Column-parallel correlated multiple sampling circuits for CMOS image sensors and their noise reduction effects," Sensors (Basel)., vol. 10, no. 10, pp. 9139-54, Jan. 2010.

Figure 5A:
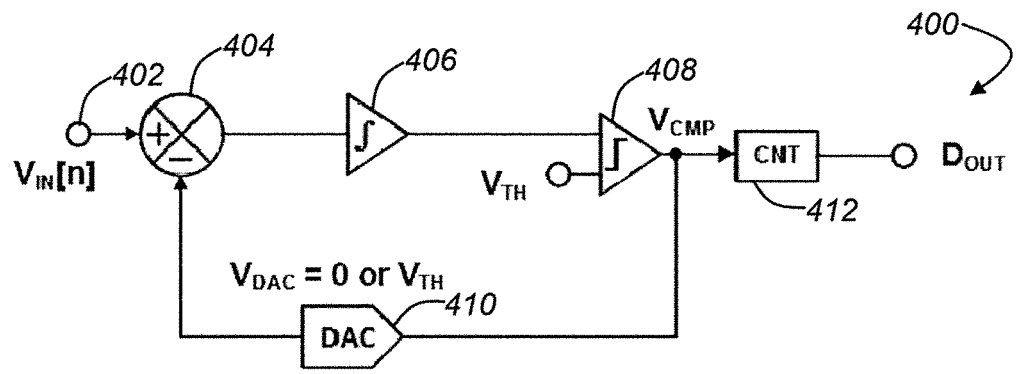
FIG. 5A illustrates one embodiment of an incremental delta-sigma ADC circuit for compressive analog-to-digital conversion.
Figure 5B:
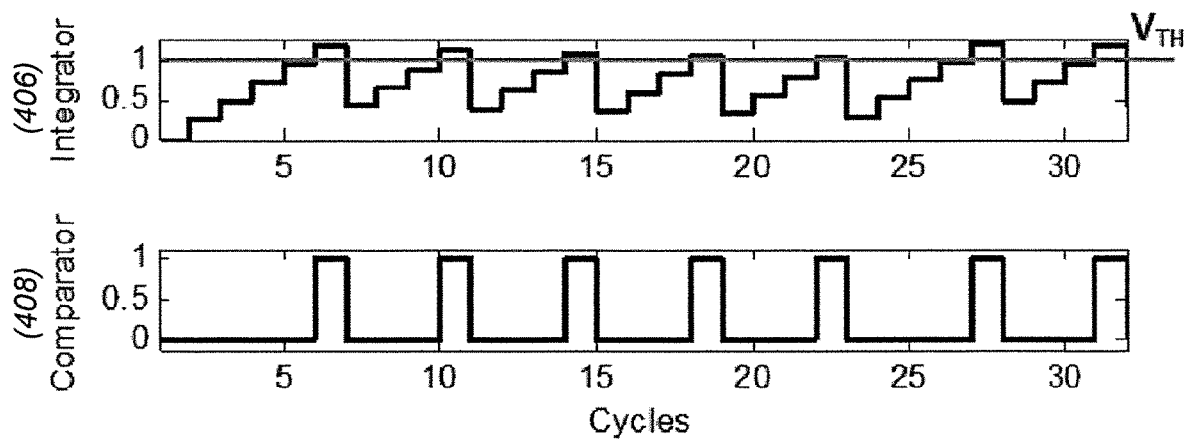
FIG. 5B depicts timing diagrams for the ADC circuit of FIG. 5A.

As an example, FIG. 5A shows an exemplary diagram of a first order incremental Sigma Delta ADC 400. The first order incremental Sigma Delta ADC comprises a $V_{IN}[n]$ input 402, a summing element 404, an integrator 406, a comparator 408, a digital-to-analog converter (DAC) 410, and a digital counter (CNT) 412. The input $V_{IN}[n]$ 402 may be sequentially applied to the integrator 406 at every cycle (e.g., the cycle number n=1 . . . 32 in this example). Whenever the integrated value exceeds $V_{TH}$, the comparator 408 provides a digital "1" as an output to the CNT 412, and $V_{TH}$ is subtracted from the integrator 406 in the next cycle. The summation of input values ($\Sigma V_{IN}[n]$) is then bound by:

$$(K+1) \cdot V_{TH} > \Sigma V_{IN}[n] > K \cdot V_{TH},$$

where, K is the quantity of digital "1s" provided by the comparator 408. The CNT counts the number of "1s" (e.g., the K-value) which is the final output $D_{OUT}$. FIG. 5B graphically illustrates a number of cycles of the integrator 406 output and comparator 408 output voltages. For example, in accordance with FIG. 5B, when the input voltage is a constant 0.24, $V_{TH}$ is 1, and the number of cycles is 32 (5-bit ADC), the value of K=7 and $\Sigma V_{IN}[n]$=0.24× 32=7.68 (7.68 being between 7 and 8 according to the expression above).

The denominator can be computed by applying the samples to the input sequentially, as explained above. However, the numerator of Equation (7) includes a multiplier (e.g., again having a range from 1 to L). Instead of implementing the multiplier, multiple sampling may be performed instead. For example, the second term in the numerator, 2·f[2] may be determined by sampling f[2] twice (e.g., f[2]+f[2]). However, as L increases, the number of samplings or the ADC cycles increases quadratically as illustrated in Equation (9), which would result in an undesirably long A/D conversion time.

$$n_{cycle} = \frac{L \cdot (L+1)}{2} \quad \text{Equation (9)}$$

Figure 6A:
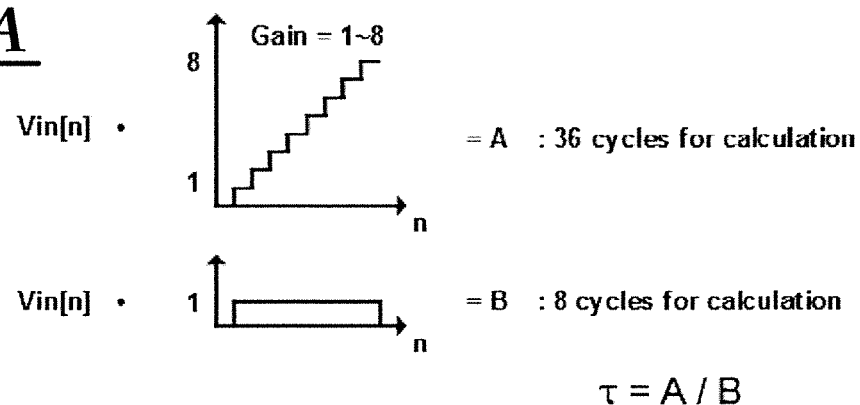
FIGS. 6A and 6B show schematic diagrams illustrating a method of simplifying a calculation of a center-of-mass method (CMM) equation.
Figure 6B:
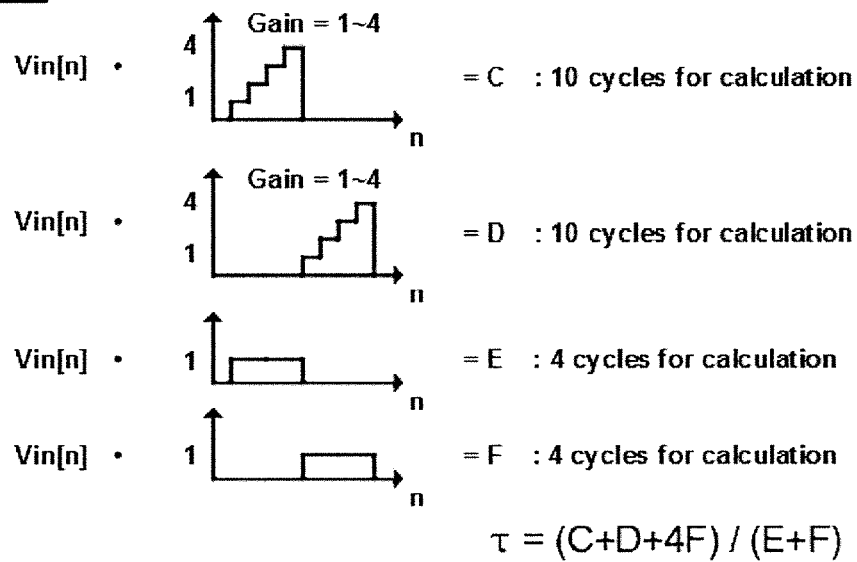

In order to reduce the number of cycles during the A/D conversion, the number of terms per summation may be divided into several groups as shown in FIGS. 6A and 6B. FIG. 6A illustrates a direct calculation of the CMM Equation of the when L=8. For example, in FIG. 6A, the calculation for numerator with L=8, A, which is the inner product of the input Vin[n] and the weight function depicted, originally required 36 cycles; however, as shown in FIG. 6B, the number of cycles may be reduced using smaller gain settings (1~4). FIG. 6B illustrates four weighted sums, $C=\Sigma_1^4 n \cdot f[n]$, $D=\Sigma_5^8(n-4)\cdot f[n]$, $E=\Sigma_1^4 f[n]$, $F=\Sigma_5^8 f[n]$ which can be used to produce the same result with the direct method in FIG. 6A; i.e., $\tau=(C+D+4F)/(E+F)$ from FIG. 6B is essentially the same as Equation (7) above. Dividing the summation into multiple terms reduces the number of ADC cycles (in this example, by 16 cycles or 36%) but increases the number of data (twice in this example) to be transmitted via I/O circuits 304. Decreasing the maximum gain (e.g., 8 to 4, or 8 to 3, etc.) in the summation may reduce ADC circuit 300 time but increase I/O circuit 304 processing times; therefore, skilled artisans will appreciate that the degree of gain reduction may be selected in a way that maximizes the overall imaging speed for a given ADC clock, for an I/O clock, and for the number L.

Next a two-step analog-to-digital conversion will be described having higher resolution and high speed. The first order incremental ADC described above and shown in FIGS. 5A to 6B serves two functions: calculating $\Sigma n \cdot f[n]$ and an analog-to-digital conversion. When L=8, the calculation requires only 36 cycles. However, 36 cycles can resolve only 36 quantization levels; this corresponds to 5.2-bit ($\log_2 36$) resolution. For even higher resolutions, an exponentially higher number of cycles is needed (e.g., for 10-bit resolution, the first-order incremental ADC requires 1024 cycles). Hereafter, a system and method will be described that avoids increasing the number of cycles and increasing ADC time in higher resolution systems.

According to one embodiment, two-step AD conversion can be utilized as in the above-noted Oike and Seo references; e.g., the two-step conversion may include a coarse conversion followed by a fine conversion. The ADC circuit 300 may begin by integrating inputs from the pixel circuits 200 in sequence to calculate the sum, performing a coarse conversion. The ADC circuit 300 has a residue which is then further quantized by the fine AD conversion for additional bits. For example, in the Oike ADC, the incremental ADC produces 7-bits for 128 cycles of input sampling. The residue value is then reapplied to the input of the ADC itself. The fine conversion provides additional 5-bits for 32 cycles. As a result, 12-bit conversion with 128 times input sampling is achieved in 160 cycles plus negligible number of additional cycles for reapplying the residue to the input. Thus, this two-step approach requires only 160 cycles as opposed to what would otherwise require 4096 cycles.

Figure 7:
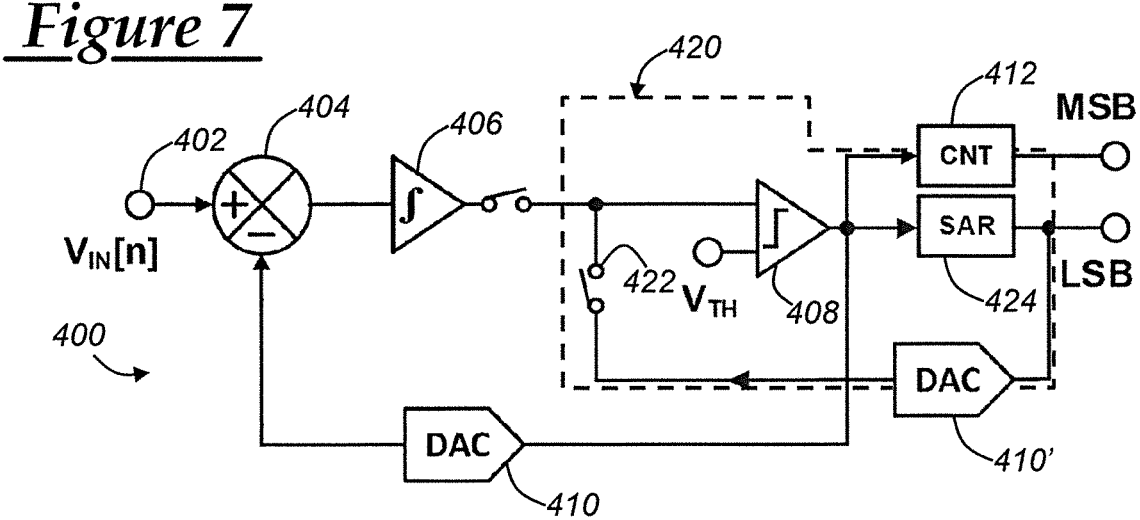
FIG. 7 illustrates an embodiment of a two-step ADC circuit for high-speed conversion.

One embodiment of a two-step coarse and fine ADC circuit 400' is shown in FIG. 7 (e.g., illustrating a two-step incremental Delta-Sigma ADC and successive approximation register (SAR) ADC); here, like reference numerals indicate identical or similar elements or similar functions. Here, the coarse (or incremental) ADC is identical to that shown in FIG. 5A, and the fine (or SAR) ADC is outlined (see box 420). Both the incremental ADC circuit and the SAR ADC circuit 420 share comparator 408. The outlined SAR ADC 420 further includes a successive approximation register (SAR) 424, a DAC 410', and a switch 422 (the comparator 408, SAR 424, DAC 410', and switch 422 being in a circuit loop). According to one embodiment, the DAC 410' of the SAR ADC circuit 420 (FIG. 7) may be substituted with a charge-redistribution DAC, as discussed below with respect to FIG. 8. As will be explained, using a charge-redistribution DAC, 5-bit fine conversion can be achieved in 5 cycles, as opposed to the 32 cycles required by [13].

Figure 8:
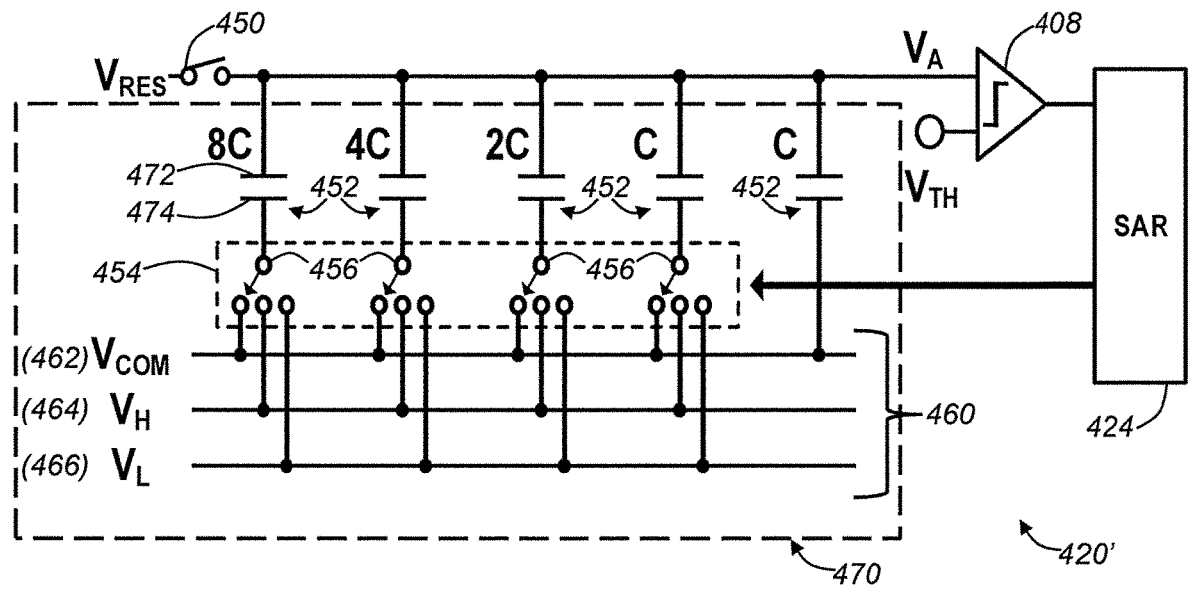
FIG. 8 illustrates one embodiment of a successive approximation register (SAR) ADC circuit that may be substituted and used with part of the ADC circuit shown in FIG. 7.

FIG. 8 illustrates one embodiment of a SAR (fine) ADC circuit 420' comprising an input switch 450 having residue voltage ($V_{RES}$), a plurality of capacitors 452 (e.g., a binary-weighted capacitor array including 8C, 4C, 2C, C, and C) arranged in parallel within a switching bank 454 (that includes a plurality of switches 456—the bank 454 coupling switches 456 to capacitors 452, i.e., 8C, 4C, 2C, C, or C), the comparator 408 (having inputs of $V_A$ and $V_{TH}$), and the SAR 424 (e.g., digital sequential logic) providing feedback to the switching bank 454. Capacitor 8C may be representative of eight times the capacitance of capacitor C (likewise, 4C may be four times C and 2C may be two times C). Each of the switches 456 enable electrical communication between the input node $V_A$ of the comparator 408 and one of three voltage reference rails 460 (depending upon SAR feedback): a common mode (average) voltage ($V_{COM}$) rail 462, a high voltage ($V_H$) rail 464, or a low voltage rail ($V_L$) 466. In this example, $V_{COM}$ is the common mode (average) voltage of $V_H$ and $V_L$ (where $V_H > V_L$).

The capacitor array 452 and switches 456 form a charge redistribution digital-to-analog converter (DAC) 470. For example, each capacitor (8C, 4C, 2C, C, or C) includes two plates (e.g., a first plate 472 and a second plate 474, the second plate being coupled to one of the reference rail(s) 460; therefore, voltage $V_A$ can be digitally changed by switching (e.g., switching the coupling between the respective second plate 474 and one of $V_{COM}$, $V_H$, or $V_L$ rails 460). For example, if the second plate 474 of the 8C capacitor changes by switching to a different reference rail (e.g., the change in voltage being illustrated as $\Delta V$), the charge stored at the node $V_A$ is changed by $\Delta Q = 8C \cdot \Delta V$; thus, $\Delta V_A = \Delta V \cdot 8C / C_{TOTAL}$ or $\Delta V/2$, where $C_{TOTAL}$ is the total capacitance of 8C, 4C, 2C, C, and C. Therefore, switching the second plate 474 voltage of 8C from $V_{COM}$ to either $V_H$ or $V_L$ changes $V_A$ by $\pm \Delta V/2$. The capacitors 4C, 2C, C can be used to control the voltage by $\pm \Delta V/4$, $\pm \Delta V/8$, $\pm \Delta V/16$, respectively. As a result, the voltage $V_A$ can be determined by Equation (10) shown below.

$$V_A = V_{RES} + \frac{\Delta V}{2}(0, \pm 1) + \frac{\Delta V}{4}(0, \pm 1) + \frac{\Delta V}{8}(0, \pm 1) + \frac{\Delta V}{16}(0, \pm 1) \quad \text{Equation (10)}$$

During operation, the residue voltage (VRES) may be sampled by opening the input switch 450. During this sampling the second plates of all capacitors may be connected initially to $V_{COM}$—thus, according to one embodiment, the initial voltage of $V_A$ may equal $V_{RES}$. As a result of the sampling process, the digital bits may be resolved successively from the most significant bit (MSB) to the least significant bit (LSB). In a first cycle, $V_A$ (initially $V_A = V_{RES}$) is compared with $V_{TH}$. Thus, output of comparator 408 is the first bit of the digital value. The SAR 424 may connect the second plate 474 of 8C to $V_H$ when $V_A < V_{TH}$ or to $V_L$ when $V_A > V_{TH}$. Ultimately, this process may attempt to adjust the $V_A$ approach to $V_{TH}$. In a subsequent cycle, $V_A$ (now altered by the switching operation) may be compared with $V_{TH}$ again. The second bit is resolved, and the SAR 424 may connect the second plate 474 of 4C (to one of voltage rails $V_H$ or $V_L$ 460) so that $V_A$ again approaches $V_{TH}$ (e.g., it is expected that this this voltage step closer to $V_A$ is smaller than in the previous step). This operation may be repeated until the desired number of bits is obtained (e.g., 5-bits).

Figure 9:
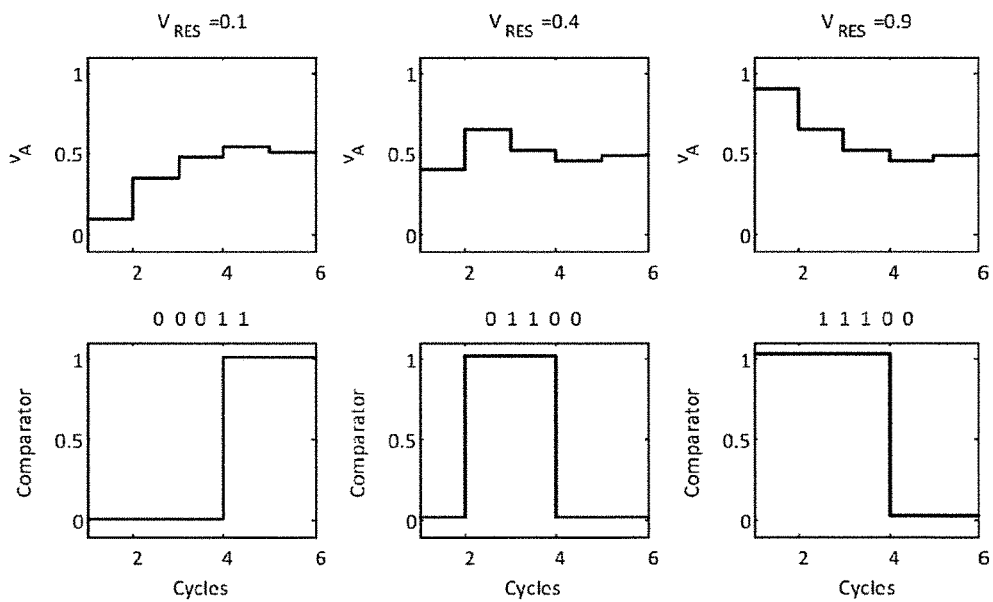
FIG. 9 illustrates graphical depictions of simulated results of the ADC circuit shown in FIG. 8.

FIG. 9 illustrates three examples of SAR conversion using the circuit shown in FIG. 8, wherein the initial value of $V_{RES}$ (and thus also the initial value of $V_A$) was 0.1V, 0.4V, and 0.9V, respectively. In this example, the values of $V_H$, $V_{COM}$, $V_L$, and $V_{TH}$ were 1V, 0.5V, 0V and 0.5V, respectively. FIG.

9 illustrates the values of $V_A$ and comparator output during the operation with three different inputs. Each A/D conversion has five comparisons and four SAR switching operations, and in each instance, the circuit resolves a 5-bit digital value and $V_A$ approaches $V_{TH}$.

It should be appreciated that other embodiments having a different quantity of capacitors may be used. As a result, a correspondingly different number of bits may be obtained. In addition, FIG. 8 illustrates one embodiment of a charge redistribution DAC 470 as an example. Other charge redistribution DAC implementations will be apparent to skilled artisans. For example, the charge distribution DAC may or may not use a binary weighted capacitor array; or e.g., a different capacitor arrangement may be used (e.g., other than a parallel capacitor array); or e.g., a different switching sequence or scheme may be used. Again, these are merely examples which may or may not be used in combination with one another, and other examples also exist.

Further, the compressive ADC circuit above has been described for use with respect to the multi-tap pixel circuit disclosed in FIGS. 2, 3A-3B; however, this was merely exemplary. For example, the compressive ADC circuit could also be disclosed with other pixel circuit implementations, including but not limited to the pixel circuit of FIG. 1A.

To achieve high photon economy, a pixel circuit having more than two taps has been disclosed that performs time-to-space conversion having a higher temporal resolution. The pixel circuit may employ more than two gates (e.g., even an order of magnitude greater than two-gate systems), unlike conventional systems.

In addition, a compressive ADC has been described enabling an increased data-rate. In one implementation, a two-step incremental Delta-Sigma ADC and an SAR ADC may be used. The compressive conversion may enable real-time imaging.

The pixel circuits and ADC circuits described herein may be used for two- or three-dimensional imaging. Likewise, the CMM equation can be used to determine time (t) in any suitable time-of-flight 3-D imaging as well.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A pixel circuit, comprising:
   a substrate body having a channel configured to be influenced by an electric field;
   an aperture in communication with the channel such that a fluorescent light input received by the aperture causes electrons to move along the channel through the substrate body in the presence of the electric field; and
   a plurality of sampling devices spaced along the channel and adapted to be switched on simultaneously so that the plurality of sampling devices collect moving electrons spatially-distributed along the channel at different locations along the same channel at the same time.

2. The pixel circuit of claim 1, wherein the substrate body comprises a p+ region in communication with an n-type region.

3. The pixel circuit of claim 1, further comprising a plurality of taps for receiving and storing the collected electrons distributed along at least a portion of the channel.

4. The pixel circuit of claim 3, wherein for each of the plurality of taps, there is an associated one of the plurality of sampling devices, wherein the plurality of taps comprises more than two taps and the plurality of sampling devices comprises more than two sampling devices.

5. The pixel circuit of claim 3, wherein the plurality of taps are coupled to an analog-to-digital (ADC) circuit that comprises:
   a coarse resolution ADC circuit that receives pixel input from the plurality of taps; and
   a fine resolution ADC circuit, wherein the fine resolution ADC circuit includes a charge redistribution digital-to-analog converter (DAC).

6. The pixel circuit of claim 5, wherein the coarse resolution ADC circuit is a Sigma Delta ADC circuit.

7. The pixel circuit of claim 5, wherein the charge redistribution DAC includes a plurality of capacitors coupled to a plurality of voltage reference rails via a switching bank.

8. The pixel circuit of claim 7, wherein a plate of each of the plurality of capacitors is coupled to the switching bank.

9. The pixel circuit of claim 1, wherein the substrate channel comprises a buried n-type channel.

10. The pixel circuit of claim 1, wherein the substrate body comprises a first p+ region comprising a first substrate contact, a second p+ region comprising a second substrate contact and spaced from the first p+ region, and a middle region disposed between the first and second p+ regions.

11. The pixel circuit of claim 10, wherein the middle region comprises a third p+ region and a buried n-type region.

12. The pixel circuit of claim 11, wherein the middle region further comprises a p-type region different from the third p+ region, and further wherein the buried n-type region is disposed between the third p+ region and the p-type region.

13. The pixel circuit of claim 12, wherein the first and second p+ regions and the p-type region of the middle region of the substrate body are configured to have a current flow between the first and second p+ regions through the p-type region to generate the electric field that causes the electrons to move along the channel.

14. A method of compression for use in fluorescence lifetime imaging, comprising the steps of:
   providing a pixel circuit, comprising: a substrate body having a channel configured to be influenced by an electric field; an aperture in communication with the channel such that a fluorescent light input received by the aperture causes electrons to move along the channel through the substrate body in the presence of the electric field; and a plurality of sampling devices spaced along the channel and adapted to be switched on simultaneously so that the plurality of sampling devices sample the collect moving electrons spatially-distributed along the channel at different locations along the same channel at the same time;

receiving at an analog-to-digital conversion (ADC) circuit an input from the pixel circuit;

determining a coarse resolution value using a coarse resolution circuit, wherein the coarse resolution includes determining a weighted sum of a finite number of samples;

determining a fine resolution value using a fine resolution circuit; and providing the fine and coarse resolution values as an output.

15. The method of claim 14, wherein determining the fine resolution value comprises using a charge redistribution digital-to-analog converter (DAC) to minimize a quantity of ADC cycles.

16. A method of compression for use in fluorescence lifetime imaging, comprising the steps of:

providing a pixel circuit, comprising: a substrate body having a channel configured to be influenced by an electric field; an aperture in communication with the channel such that a fluorescent light input received by the aperture causes electrons to move along the channel through the substrate body in the presence of the electric field; and a plurality of sampling devices spaced along the channel and adapted to be switched on simultaneously so that the plurality of sampling devices sample the collect moving electrons spatially-distributed along the channel at different locations along the same channel at the same time;

receiving at an analog-to-digital conversion (ADC) circuit an input from the pixel circuit;

determining a coarse resolution value using a coarse resolution circuit;

determining a fine resolution value using a fine resolution circuit, wherein determining the fine resolution value comprises using a charge redistribution digital-to-analog converter (DAC) to minimize a quantity of ADC cycles; and providing the fine and coarse resolution values as an output.

* * * * *